United States Patent
Kerstan et al.

(10) Patent No.: US 6,888,637 B2
(45) Date of Patent: May 3, 2005

(54) GAS SAMPLE VESSEL FOR A GAS ANALYZER

(75) Inventors: Felix Kerstan, Jena (DE); Werner Hoyme, Jena (DE); Nico Correns, Weimar (DE); Ullrich Klarner, Jenapriessnitz (DE)

(73) Assignee: Carl Zeiss Jena GmbH, Jena (DE)

( * ) Notice: Subject to any disclaimer, the term of this patent is extended or adjusted under 35 U.S.C. 154(b) by 251 days.

(21) Appl. No.: 10/302,180

(22) Filed: Nov. 22, 2002

(65) Prior Publication Data

US 2003/0103204 A1 Jun. 5, 2003

(30) Foreign Application Priority Data

Nov. 22, 2001 (DE) .......................................... 101 57 275

(51) Int. Cl.[7] .............................................. G01N 21/00
(52) U.S. Cl. ...................................... 356/440; 356/244
(58) Field of Search ................................ 356/432–442, 356/244, 246; 250/576, 343, 428, 277.11, 277.21

(56) References Cited

U.S. PATENT DOCUMENTS

| 3,795,450 | A | * | 3/1974 | Munk .......................... 356/246 |
| 3,998,557 | A | * | 12/1976 | Javan .......................... 356/434 |
| 4,188,126 | A | * | 2/1980 | Boisde et al. ................ 356/440 |
| 4,747,687 | A | * | 5/1988 | Hoppe et al. ................ 356/246 |
| 4,822,166 | A | * | 4/1989 | Rossiter ....................... 356/246 |
| 4,988,195 | A | * | 1/1991 | Doyle .......................... 356/244 |
| 5,184,192 | A | * | 2/1993 | Gilby et al. ................. 356/246 |
| 5,432,610 | A |   | 7/1995 | King et al. |
| 5,450,193 | A |   | 9/1995 | Carlsen et al. |

* cited by examiner

*Primary Examiner*—Frank G. Font
*Assistant Examiner*—Sang H. Nguyen
(74) *Attorney, Agent, or Firm*—Reed Smith LLP

(57) ABSTRACT

A gas sample vessel for a gas analyzer comprising a housing enclosing a cylindrical resonator cavity. Two mirrors which limit the resonator cavity are fastened to the housing for coupling in and feeding back the measurement light proceeding from an illumination source. The mirrors are curved concavely at their surfaces facing the housing and the housing is curved convexly at its surfaces facing the mirrors with approximately the same radius of curvature. The centers of curvature lie in the center axis of the resonator cavity and the mirror surfaces of the mirrors are portions of the concavely curved surfaces facing the housing.

11 Claims, 2 Drawing Sheets

GAS SAMPLE VESSEL FOR A GAS ANALYZER

CROSS-REFERENCE TO RELATED APPLICATIONS

This application claims priority of German Application No. 101 57 275, filed Nov. 22, 2001, the complete disclosure of which is hereby incorporated by reference.

BACKGROUND OF THE INVENTION a) Field Invention of the Invention

The invention is directed to a gas sample vessel for a gas analyzer comprising a housing enclosing a cylindrical resonator cavity, two mirrors which limit the resonator cavity being fastened to the housing for coupling in and feeding back the measurement light proceeding from an illumination source.

b) Description of the Related Art

Measuring devices known as gas analyzers are used to determine the properties of a gas. Gas analyzers frequently have a cavity resonator, as it is called, which receives a gas sample and into which a light beam is coupled in a defined manner. The propagation of the light within the cavity is influenced depending on the properties of the gas. This influence is evaluated (intracavity gas analysis).

Resonators with cylindrical cavities limited at both ends of their longitudinal extension by mirrors with spherically curved mirror surfaces are known. A recurring problem in the production of resonators of this type consists in adjusting the mirrors in such a way that the reflected radiation is directed exactly in the center axis of the cylindrical cavity.

Gas analyzers of the type mentioned above are described in U.S. Pat. Nos. 5,432,610 and 5,450,193. These gas analyzers have sample chambers formed from a pipe piece which is provided with a mirrored inner wall and which is defined at both ends by mirrors whose position is adjustable. Through one of these mirrors, the in-coupling mirror, the measurement light beam coming from a laser light source reaches the interior of the gas sample chamber.

The coupled-in laser beam extends in the center axis of the gas sample vessel and it is necessary to adjust the mirrors in such a way that their focal point lies in the center axis.

Additional auxiliary devices are needed during adjustment to move and hold the individual elements because both the in-coupling mirror and the opposite end mirror must be moved relative to the pipe piece in several degrees of freedom for exact orientation and, finally, must be held in the correct position until fixed.

OBJECT AND SUMMARY OF THE INVENTION

On this basis, it is the primary object of the invention to reduce the expenditure on adjustment of the mirrors in the manufacture of gas sample vessels of the type mentioned above.

According to the invention, in a gas sample vessel of the type described at the outset, the mirrors are curved concavely at their surfaces facing the housing and the housing is curved convexly at its surfaces facing the mirrors with approximately the same radius of curvature, the centers of curvature lie in the center axis of the cylindrical resonator cavity and the surfaces of the mirrors are portions of the concavely curved surfaces facing the housing.

Due to the spherical shape of the surfaces adjoining the mirrors and housing, adjustment takes place automatically already at the moment that the mirrors are arranged at the housing such that the centers of curvature of the mirror surfaces lie in the longitudinal axis and center axis of the cylindrical cavity and, therefore, in the beam path of the measurement light as is required. Further orientation is unnecessary. The mirrors need only be fixed in position, e.g., by means of glue.

The radius of curvature provided at the housing is preferably slightly greater than the associated radius of curvature at the mirror surfaces. In this way, an outer annular edge of the curved mirror surfaces rests on the associated housing surface, which is likewise curved, and the mirrors accordingly have a stable position relative to the housing. Conversely, if the radius of curvature of the mirror surface were greater than the associated radius of curvature at the housing, this would result in point contact of the mirror with a risk of tilting before fixing could be carried out. This should be prevented.

Accordingly, in contrast to the prior art, additional auxiliary devices and displacing movements are no longer necessary for adjusting the mirrors.

For example, the mirror through which the measurement light is coupled in is first arranged and fixed during assembly. The opposite mirror is then fastened and the cavity is oriented relative to the beam path of the measurement light.

In order to allow the gas sample to enter and exit, the resonator cavity is provided in the area between the two mirrors with a gas inlet connection piece and a gas outlet connection piece, both of which can be oriented vertical to the center axis.

The housing is preferably formed in one piece from a transparent tube, preferably a quartz glass tube, with a highly reflecting surface.

In an alternative construction, the housing is formed in multiple pieces from a transparent tube, preferably a highly reflecting quartz glass tube, and a high-grade steel sleeve at its surface.

The first variant has proven more favorable, since mirroring the surface is less costly than producing and arranging a highly reflecting sleeve in the interior of the housing.

Further, there is a preferred variant of the arrangement according to the invention in which the illumination source is connected directly to the in-coupling mirror. This virtually prevents misalignment of the laser beam during the detection of measurement values due to shaking, for example. Further, this arrangement offers the possibility of all-purpose use at different measurement locations without readjustment of the individual elements.

For purposes of sealing and fixing the mirrors at the housing, bevels are worked in so as to form gluing gaps. By completely filling up the gluing gaps with an optical glue, the sample can be prevented from exiting the resonator cavity in an unwanted manner and can also be prevented from escaping between the mirror systems and the resonator cavity in so-called dead spaces, which could possibly corrupt the measured values.

Due to the fact that the mirrors are fixedly connected to the housing of the resonator cavity to form a component group, no additional receptacles or holders are required for fixing the individual elements in their adjusted position during the measurement process.

The gas sample vessel according to the invention will be described more fully with reference to an embodiment example shown in the following.

DESCRIPTION OF THE PREFERRED EMBODIMENTS

Figure 1:
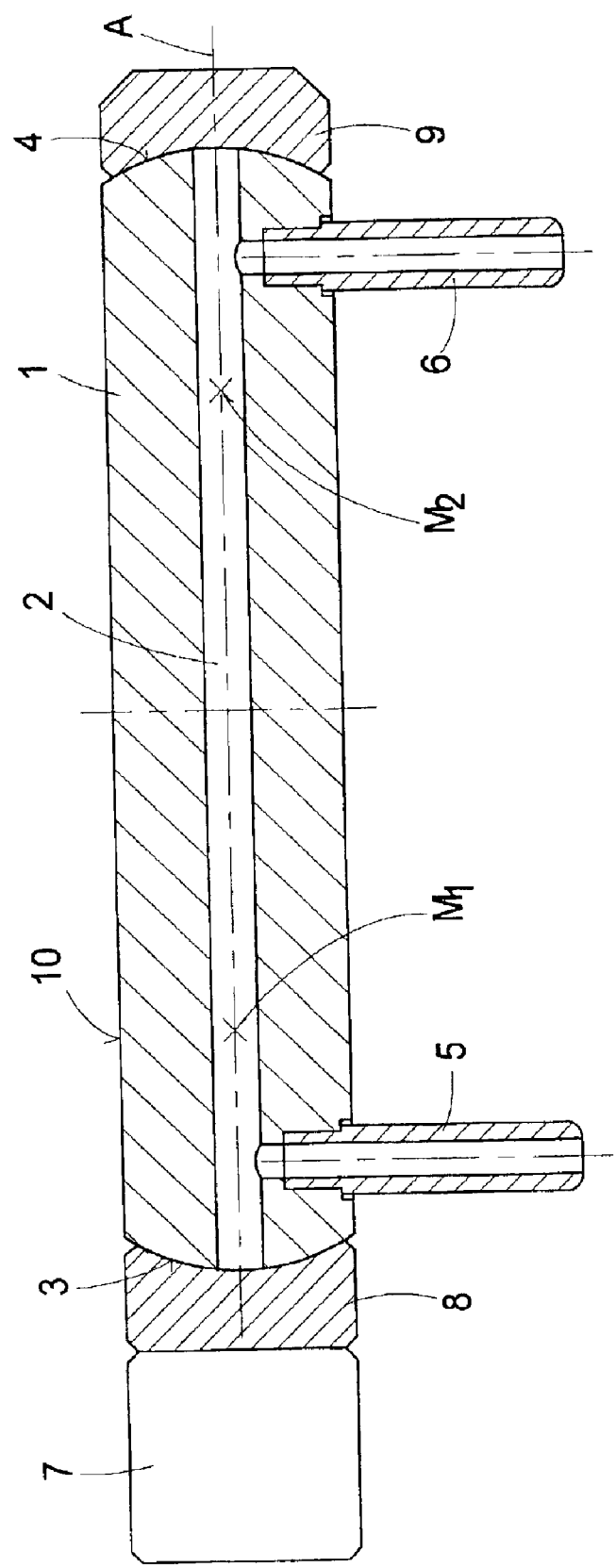
FIG. 1 shows a cylindrical housing 1 which is made of quartz glass and has the resonator cavity 2 with center axis A serving to receive a gas sample.

It can be seen in FIG. 1 that surfaces 3, 4 are formed at both ends of the resonator cavity 2 and are spherically curved in convex manner. The centers of curvature M1 and M2 lie in the center axis A.

A gas inlet connection piece 5 and a gas outlet connection piece 6 are fixedly arranged in the housing 1 vertical to the center axis A.

Mirrors 8 and 9 are arranged at the surfaces 3, 4 of the housing 1 so that the measurement light beam proceeding from a laser 7 can enter the resonator cavity and so that the radiation can be fed back. In this case, for example, the mirror 8 is connected directly to the laser 7.

Figure 2:
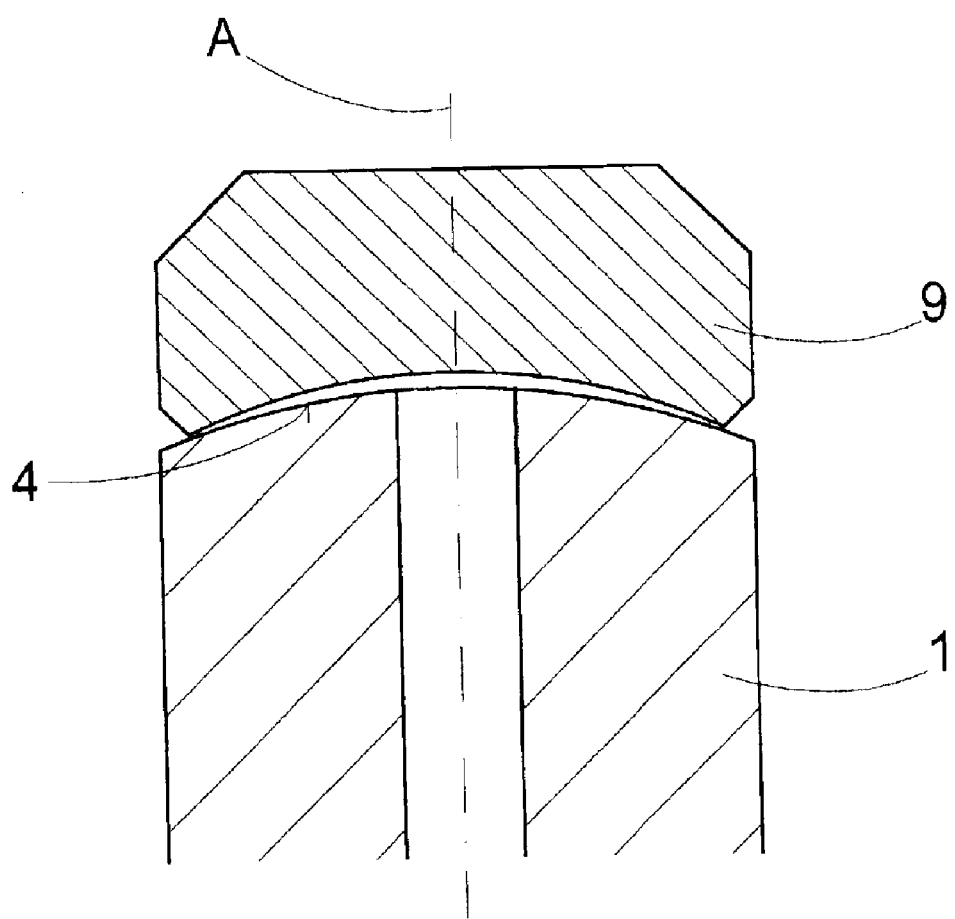
FIG. 2 shows a closer view of the contact of a mirror surface at an associated housing surface.

The surfaces of the mirrors 8, 9 facing the housing 1 are likewise spherical, but are curved concavely. The radii of curvature of the mirrors 8, 9 are preferably somewhat smaller than the radii of curvature of the surfaces 3, 4, resulting in the contact of a curved mirror surface at the housing surface, which is likewise curved, as is shown in the enlarged view in FIG. 2. In this way, the centers of curvature of the arranged mirrors 8, 9 and the centers of curvature M1, M2 lie in the center axis A.

The advantage resulting from the fact that the radius of curvature provided at the mirror surface is constructed so as to be slightly smaller than the associated radius of curvature at the housing 1 is that the curved mirror surfaces rest on the associated curved housing surface 3, 4 by an annular outer edge and the mirrors accordingly have a stable position relative to the housing. This also prevents a situation in which the housing radius is less than the mirror radius due to manufacturing tolerances which causes the mirror to occupy an unstable position during assembly.

During assembly, for example, the mirror 8 used for coupling in the measurement light beam is first placed on the spherically formed surface 3 of the housing 1 and is fixed by means of a gluing agent. No additional auxiliary devices are needed to enable the center of curvature M1 to lie in the center axis A.

The mirror 9 is first placed on surface 4 and is fixed at the latter and the component group formed of the laser 7 and mirror 8 is also produced. The component group formed of laser 7 and mirror 8 is then arranged and fixed at the surface 3.

As has already been shown, wasteful adjustment steps for positioning the mirrors 8, 9 are obviated by the design of the limiting surfaces between the mirrors 8, 9 and the housing 1. The circumferential surface 10 of the housing 1 is advantageously provided with a mirror coating which reflects toward the inside.

While the foregoing description and drawings represent the present invention, it will be obvious to those skilled in the art that various changes may be made therein without departing from the true spirit and scope of the present invention.

REFERENCE NUMBERS

| | |
|---|---|
| 1 | housing |
| 2 | resonator cavity |
| 3, 4 | surfaces |
| 5 | gas inlet connection piece |
| 6 | gas outlet connection piece |
| 7 | laser |
| 8, 9 | mirrors |
| 10 | circumferential surface |
| A | center axis |
| M1, M2 | centers of curvature |

What is claimed is:

1. A gas sample vessel for a gas analyzer comprising:
   a housing enclosing a cylindrical resonator cavity having a center axis;
   two mirrors which limit the resonator cavity being fastened to the housing for coupling in and feeding back the light proceeding from an illumination source;
   the surfaces facing the housing for said mirrors being curved concavely;
   the surfaces facing the mirrors for said housing being curved convexly with approximately the same radius of curvature;
   corresponding centers of curvature lying in the center axis of the cylindrical resonator cavity; and
   mirror surfaces of the mirrors being portions of the concavely curved surfaces facing the housing.

2. The gas sample vessel according to claim 1, wherein the radii of curvature of the mirrors are slightly less than the radii of curvature of the associated surfaces.

3. The gas sample vessel according to claim 1, wherein the resonator cavity is provided in the area between the two mirrors with a gas inlet connection piece and a gas outlet connection piece.

4. The gas sample vessel according to claim 1, wherein the housing is formed in one piece from a transparent tube, with a highly reflecting surface.

5. The gas sample vessel according to claim 4, wherein the transparent tube is a quartz glass tube.

6. The gas sample vessel according to claim 1, wherein the housing is formed in multiple pieces from a transparent tube, and the surface of the housing has a highly reflecting high-grade steel sleeve.

7. The gas sample vessel according to claim 6, wherein the transparent tube is a quartz glass tube.

8. The gas sample vessel according to claim 1, wherein a laser is provided as illumination source and is directly connected to one of the mirrors.

9. The gas sample vessel according to claim 1, wherein the mirrors are fixed at the housing by glue.

10. A gas sample vessel for a gas analyzer comprising:

first and second mirrors each having a spherically curved concave surface; and a housing enclosing a cylindrical resonator cavity having a center axis, the housing having:

a first end having a curved convex surface and facing the curved concave surface of the first mirror; and a second end having a curved convex end facing the curved concave surface of the second mirror;

wherein the first and second ends and the first and second mirrors all have approximately the same radius of curvature and all have centers of curvature lying in the center axis of the cylindrical resonator cavity.

11. The gas sample vessel according to claim 10, wherein the radii of curvature of the first and second mirrors are slightly less than the radii of curvature of the first and second ends such that the first and second mirrors are disposed on an annular outer edge of the first and second ends.

* * * * *